United States Patent [19]

Woo

[11] 4,166,381
[45] Sep. 4, 1979

[54] APPARATUS FOR DETERMINING THE VISCOSITY OF FLUIDS

[75] Inventor: Lecon Woo, Wilmington, Del.

[73] Assignee: E. I. Du Pont de Nemours and Company, Wilmington, Del.

[21] Appl. No.: 880,943

[22] Filed: Feb. 24, 1978

[51] Int. Cl.² ................................................. G01N 11/00
[52] U.S. Cl. ........................................................ 73/54
[58] Field of Search ................................. 73/54, 60, 59

[56] References Cited

U.S. PATENT DOCUMENTS

| | | | |
|---|---|---|---|
| 3,194,064 | 7/1965 | Miles | 73/54 X |
| 3,349,604 | 10/1967 | Banks | 73/32 A |
| 3,382,706 | 5/1968 | Fitzgerald et al. | 73/59 |
| 3,710,614 | 1/1973 | Oppliger | 73/59 |
| 3,712,117 | 1/1973 | Fitzgerald et al. | 73/59 |
| 3,751,977 | 8/1973 | Schilling, Jr. | 73/101 |
| 3,762,429 | 10/1973 | Fitzgerald et al. | 137/92 |
| 3,864,961 | 2/1975 | Cessna, Jr. | 73/54 |
| 4,034,602 | 7/1977 | Woo et al. | 73/15.6 X |

FOREIGN PATENT DOCUMENTS

| | | | |
|---|---|---|---|
| 43-28400 | 12/1968 | Japan | 73/54 |
| 814155 | 5/1959 | United Kingdom | 73/60 |

OTHER PUBLICATIONS

*Weissenberg Rheogoniometer*, In Sangamo Weston Controls Ltd. brochure.

Primary Examiner—S. Clement Swisher
Assistant Examiner—Joseph W. Roskos

[57] ABSTRACT

The apparatus described includes a fixed plate and a movable plate mounted to vibrate relative to the fixed plate in a plane parallel to the plane of the fixed plate. The plates are spaced apart so that fluid can be placed therebetween. A drive system maintains the movable plate vibrating at its resonant frequency. The drive system uses a sinusoidal drive with a linear transducer to facilitate determination of viscosity simply by measuring the peak driving force.

7 Claims, 5 Drawing Figures

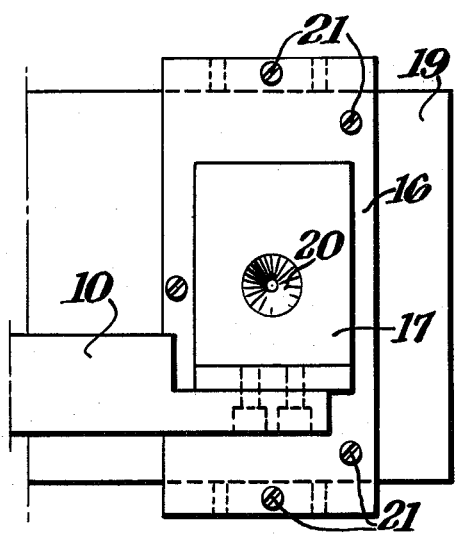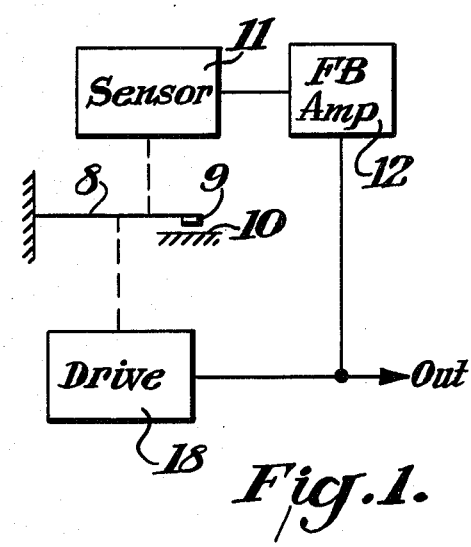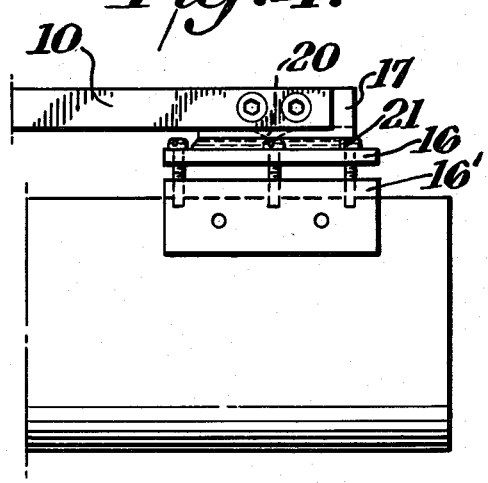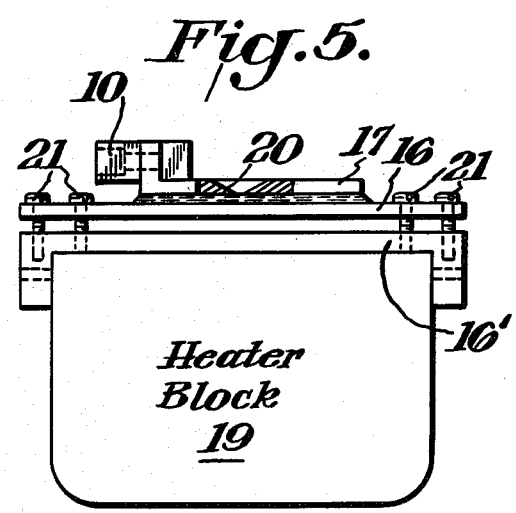

APPARATUS FOR DETERMINING THE VISCOSITY OF FLUIDS

CROSS REFERENCE TO RELATED APPLICATIONS

This application is related to an application Ser. No. 880,944, filed Feb. 24, 1978, by Lecon Woo titled Method and Apparatus for Measuring the Loss Modulus of Materials and assigned to the same assignee as this application.

DESCRIPTION

TECHNICAL FIELD

This invention relates to an apparatus for measuring the viscosity of fluid materials.

BACKGROUND ART

Many different devices have been developed for the purpose of measuring the viscosity of fluids. Many of these devices have vibrated a test rod or similar device in the fluid, rotated a test probe in a fluid, or used similar techniques. Typical of these prior art techniques are those described in U.S. Pat. Nos. 3,382,706; 3,762,429; 3,712,117 and 3,710,614. A major disadvantage of these techniques is that the test probe itself is affected by the density of the fluid under test as well as by the viscosity. This tends to cause some error in the measurement. An additional problem that occurs in devices of this type is that, although the basic definition of viscosity requires that the shear between two parallel plates, caused by the fluid, be measured, there is no readily available second plate with which to reference the shear waves. These factors tend to reduce the accuracy and reliability of measurements of this type.

Another viscometer known in the prior art is that described in U.S. Pat. No. 3,349,604. In this viscometer, changes in the resonant frequency of a vibrating probe disposed in the fluid are measured to provide an indication of the viscosity of the fluid itself. A disadvantage of this system is, as noted above, that the vibrational frequency is effected not only by the viscosity but also by the density of the fluid. This tends to introduce unwanted errors is measurement.

Another known type of viscometer or rheogoneometer uses rotating or oscillatory plates with the fluid disposed between the plates. The energy transferred from the first to the second plate is measured to provide an indication of the viscosity of the fluid disposed between the plates. While this is an apparatus which has many advantages over those described above, it nevertheless suffers from the disadvantage that it is not entirely accurate for the reason that it does not directly measure the shear, but rather measures a factor, energy transfer, which is the result of shear.

Accordingly, it is an object of this invention to obviate many disadvantages of the prior art viscometers.

Another object of this invention is to provide an improved apparatus for measuring the viscosity of fluids.

DISCLOSURE OF INVENTION

According to the invention, an apparatus for the measurement of the viscosity of fluid materials comprises a fixed plate, a flexible vibratory means, a movable plate mounted on the vibratory means for vibratory movement in a plane parallel to a common plane which is parallel to the plane of the fixed plate, said plates being spaced apart to receive the fluid material therebetween, drive means for maintaining said vibratory means in vibration at its resonant frequency using a sinusoidal driving force, and means for measuring said driving force.

In accordance with one aspect of the invention, the movable plate is mounted on a pivoted arm wherein the pivot is a flexure pivot having a known spring constant.

BRIEF DESCRIPTION OF THE DRAWINGS

FIG. 1 is a block diagram of a generalized apparatus for measuring viscosity constructed in accordance with this invention;

FIG. 3 is a partial plan view of the fixed and movable plates used in the apparatus of FIG. 2;

FIG. 4 is a partial side elevation view of the fixed and movable plates used in the apparatus of FIG. 2; and FIG. 5 is an end elevation view of the fixed and movable plates employed in the apparatus of FIG. 2.

BEST MODE FOR CARRYING OUT THE INVENTION

Figure 2:
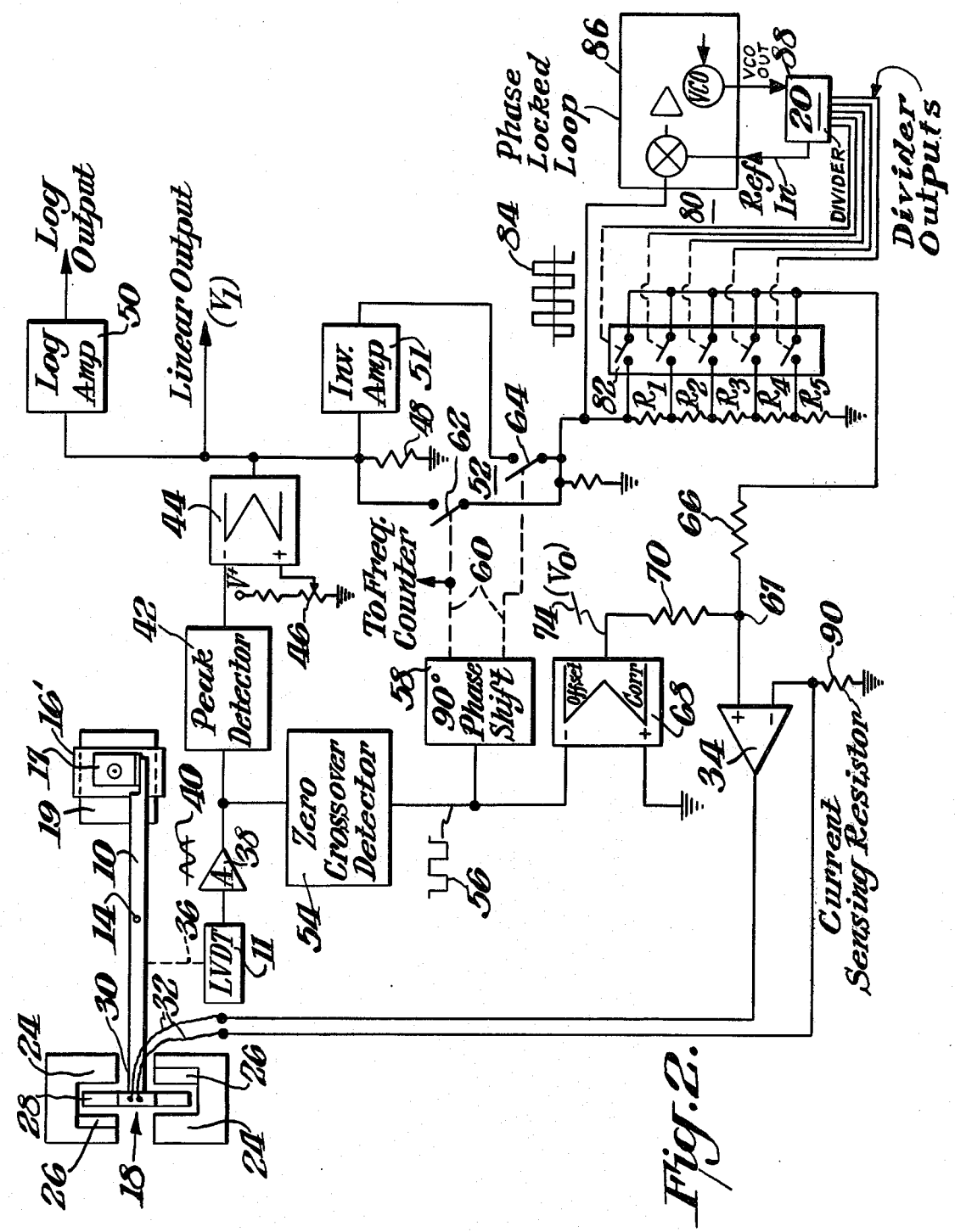
FIG. 2 is a partial block partial schematic diagram of a driving apparatus constructed in accordance with a preferred embodiment of this invention for measuring the viscosity of fluid materials.

The apparatus of this invention may find use with the electronic drive system, which provides a linear sinusoidal drive for maintaining a dynamic mechanical system in oscillation, that is described in U.S. Pat. No. 4,034,602 issued to Woo et al. and assigned to the same assignee as this application. The apparatus that is seen in FIG. 1 includes a vibrating tyne 8 fixed at one end with a movable plate 9 at the other. The movable plate is adapted to vibrate in a plane parallel to the plane of a fixed plate 10. Fluid to be tested is placed between the plates. The arm 8 is driven by a linear sinusoidal drive system which includes an electromechanical driver 18. Movement of the arm 8 is sensed by a position transducer or sensor 11 whose output is coupled through a feedback amplifier 12 to the driver 18. In this manner the arm is maintained in oscillation or vibration at the resonant frequency of the system.

The details of a preferred system of this type are shown in FIG. 2. In FIG. 2 the arm 10 is a vibrating, pivoted sample arm pivotally mounted at its central portion by a flexure pivot 14. Typically, the flexure pivot may have a sufficiently high stiffness such that the vibrating arm has a natural frequency of about 36 Hz although other frequencies may be used as desired. Shear plates 16, 17 of various areas can be attached to the tip of the arm and a stationary heater block 19. The stationary plate 16 can be adjusted in height so as to vary the gap or spacing between the plates and is mounted on the frame or heater block 19 of the apparatus so that viscosity can be determined at varying temperatures. The sample gap spacing may be set by adjusting the position of the stationary plate as by the adjusting screws 21 or any other means such as rack and pinion.

The movable plate 17 has a central hole or orifice 20 to accommodate the introduction of the sample fluid thereto such that it may spread between the two plates. The fixed or stationary plate 16 has a base 16' which may be U-shaped and fits over the heater block. It may be secured thereto as by screws. The adjusting screws 21 actually engaged the base 16'. Thus, the oscillatory motion occurs in a common plane, both the fixed and movable plates being parallel to this common plane such that the fluid is subjected to shear in conformity with the definition of viscosity, which is essentially defined as the force on a one square centimeter plate with a velocity gradient of one centimeter per second per centimeter. In such a system, the driving force at any instant can be described as $$I\ F(t) = \eta \cdot \beta \cdot \dot{\chi}$$

where
$\eta$ = viscosity
$\beta$ = form factor, = (area/gap) = (A/h)
$\dot{\chi}$ = relative velocity of two plates so $$F(t) = \eta A/h \cdot \epsilon_1 \omega \cos \omega t$$

and with apparatus damping Fa, $$F(t) = \epsilon_1 \omega \cos \omega t \times \left[ \frac{\eta A}{h} + Fa \right]$$

In this formula, the various symbols are
F: driving force (dyne)
$\eta$: sample viscosity (poise, dyne sec cm$^{-2}$)
A: Area (cm$^2$)
h: gap (cm)
$\epsilon_1$: peak displacement (cm)

In other words, by measuring peak driving force in which a sinusoidal drive is used, sample viscosity can be simple measured. A drive system for accomplishing that is the same as that described in a copending application Ser. No. 880,944, filed Feb. 24, 1978, by Woo. As is described in this Woo application, a linear drive system is employed and incorporates a pair of U-shaped iron pole pieces 24, a permanent magnet such as a ferrite magnet 26 disposed in the air gap provided by the pole pieces 24 and the magnets 26. The pancake coil 28 is a uniformly wound, flat coil secured to the driven end 30 of the driving arm 10. Lead wires 32 from the pancake coil are connected to a drive amplifier 34 which supplies the necessary current for causing the coil to move within the magnetic field (at right angles to the field) and thereby cause a vibratory or oscillatory motion of the driving arm 10 about the flexure pivot 14, as will be described. The frequency of the oscillation is primarily determined by the spring constant of the pivot. By changing to pivot of different spring constants, a different frequency can be obtained.

This mechanical motion of the arm 10 is sensed by a suitable displacement transducer 11 which may be any of those well known in the art. Preferably, this transducer may be a linear voltage differential transformer of known type which is mechanically coupled as depicted by the dashed line 36 to the driving arm 10. As is known, a linear voltage differential transformer displacement transducer provides an output voltage signal which varies in amplitude and frequency in accordance with the movement of the arm 10 whose displacement is being sensed. This displacement signal is amplified by an amplifier 38 to provide an alternating waveform such as is depicted by the curve 40. The amplifier displacement signal 40 is passed to a peak detector 42 which provides a direct current output signal varying in amplitude in accordance with the peak amplitudes of the signal 40. This peak detected signal is coupled to the negative-going input of a gain control integrator 44 so that it may be compared with a predetermined reference level, such as is established by a potentiometer voltage divider 46, which is applied to the positive-going input of the same integrator. Thus, the output of the integrator 44 will be a relatively constant voltage level or analog signal which is developed across an output resistor 48. By proper adjustment of the voltage divider 46, the analog signal developed across the output resistor 48 may be related to the power required in the system to maintain the amplitude of the mechanical vibrations or oscillations constant. Thus, by time switching the analog signal and using the switched signal to drive the system, the amplitude of the oscillations of the arms is maintained constant. Also, by amplifying it using any suitable type of logarithmic amplifier 50, the dynamic range of the output is enhanced. The analog signal $V_1$ developed across the output resistor 48 is coupled through a switching circuit 52 and a switched divider network 80 to drive amplifier 34, which energizes the drive transducer 18 to maintain the mechanical system in oscillation.

The switching circuit 52 functions, as will be described, to maintain the signals applied to the drive amplifier 34 in-phase with the vibratory motion of the mechanical system. This is accomplished by a zero crossover detector 54, which is a high gain amplifier that shapes, due to its high gain, the signals into a rectangular waveform 56. Hereinafter such amplifiers will be referred to as squaring amplifiers. The vertical going components of the waveform 56 correspond in time to the zero crossover points of the displacement signal 40. This rectangular signal is sent through a 90° phase shifter 58, which may be of conventional design, to change the phase of this rectangular signal 56 such that the zero crossovers correspond in time to the peaks of the displacement signal 40. It is these phase shifted signals which are used to control the switching circuitry 52. This phase shift circuit 58 has outputs depicted by the dashed lines 60 which may be relays but preferably are analog switches 62 and 64, respectively. These analog switches may be of a known type, such as integrated circuit chips MC 1401 CP. To this end, the first switch 62 connects the analog voltage $V_1$ across the resistor 48 through the divider network 80, as will be described, and a summing resistor 66 to a summing point 67 which is the input of a drive amplifier 34. In like manner, the voltage across the resistor 48 is coupled through an inverting amplifier 51 of conventional design, the second analog switch 64, the divider network 80, and the summing resistor 66 to the summing point 67. The output to the switching circuitry is a square wave depicted by the waveform 84.

There is provided an offset correction circuit which receives the rectangular waveform 56 and automatically adjusts the drive voltage of the mechanical system. This offset correcting circuit may include an integrating circuit 68 in which case the rectangular waveform 56 is applied to the negative-going input of the integrator and the positive-going input is referenced to ground. The output of this integrator is thus a signal whose level varies in accordance with the asymmetry of the signal derived from the displacement transducer 20. This asymmetry may be due to asymmetrical placement of the transducer itself or asymmetrical vibration due to a misaligned drive system. In any event, any asymmetry in the system, as manifested in the displacement waveform, will be corrected by the integrator 68 by changing the level of the voltage of which is coupled through a summing resistor 70 to the summing point 67. The offset signal is a slowly varying DC level, depicted by the waveform 74, and is combined with the switched voltages from the analog signal developed across resistor 48 to control the operation of the drive transducer 18. The offset correction integrator 68 adjusts the displacement waveform 40 such that the crossover times are equally spaced, i.e., symmetrical in time.

The square wave signals from the switches 52 are coupled through the switched divider network 82, which functions as a sine wave synthesizer circuit to convert the square waves into sinusoidal waves prior to application to the resistor 66. Five resistors R1, R2, R3, R4 and R5, which are selected in value to conform to various equally spaced in time points between 0 and $\pi/2$ of sinusoidal waveform are connected in series from the switches 52 to ground. Each resistor is bypassed by an FET transistor switch 82. These switches 82 are triggered in sequence at a rate twenty times the frequency of the square wave 84 (the oscillatory system frequency). This switching frequency is obtained by coupling the square wave 84 also to a phase locked loop 86 whose VCO is coupled to a divider (by twenty) 88 which provides series of a five output switching pulses on each of five output lines which drive the FET switches 82. The phase locked loop may be an RCA CD4046, the divider RCA CD4017 and CD4027, the FET switches RCA CD4016.

In this manner the square wave 84 is converted, by the switched attenuator provided by the resistors R1 to R5, into a sine wave approximated by twenty segments using only five resistors and five semiconductor devices. A further advantage is that the integrity of the drive circuits permits the phase and amplitude information to be preserved. Since the drive is now a sine wave signal that is located 90° out of phase with the position or displacement signals 40, the sine wave drive signal is in-phase with the sample's dissipation function. Also, since the current flowing through the coil is directly proportional to the input voltages applied to the drive amplifier, the force that is imparted to the sample-apparatus system equals KV, where K is a constant for given driver and is made up from contribusions such as magnetic field intensity, number of turns in the coil and the like. The voltage V is the input voltage which may be measured directly using a current sensing resistor 90 tapped off the drive coil. The calibration constant K can be determined by using precisely known weights attached to the movable plate when in a vertical movement plane and measuring the restoring voltage.

In operation, the sample gap spacing is determined by the distance between the moving plate 17 and the stationary plate 16 which typically can vary between 0 and 0.15 cm. Before introducing a sample between the plates 16, 17, the drive force required to maintain oscillation for the free pivot system at different amplitudes is first determined. This level is subtracted from the sample viscosity determinations. Next, a fluid sample is introduced between the plates by introducing it into the orifice 20. The system is now energized and the driving force required to maintain the system in oscillation measured. This driving force in the system having the linear sinusoidal drive is now a measure of the viscosity which may be computed simply by introducing this force, or its related voltage, measurement into the viscosity formula noted above. This apparatus is particularly advantageous because of its simplicity and the minimal calibrations that are required. The apparatus is independent of the fluid density being measured and dependent essentially only upon the viscosity of the fluids. Plates with different sized areas may be readily attached to the vibrating arm to accommodate different materials. The use of the linear sinusoidal drive together with plates which simulate the motion specified by the very definition of viscosity permit accurate repeatable viscosity measurements to be made.

I claim:

1. An apparatus for the measurement of the viscosity of fluid materials comprising, in combination:
   a fixed plate;
   a flexible vibratory means;
   a movable plate mounted on said vibratory means for vibratory movement in a plane parallel to the plane of said fixed plate;
   said plates being parallel and spaced apart to receive said fluid materials therebetween;
   drive means for maintaining said vibratory means in vibration at its resonant frequency using a sinusoidally varying driving force; and
   means for measuring said driving force.

2. The apparatus of claim 1 wherein said vibrating means includes an elongated member with said movable plate mounted thereon.

3. The apparatus of claim 2 which also includes flexure pivots for mounting said elongated member for pivotal motion in a plane parallel to the plane of said movable plate.

4. The apparatus of claim 3 wherein said flexure pivots have a known spring constant.

5. The apparatus of claim 4 wherein said movable plate is located above said fixed plate and defines a hole therein to accommodate said fluid materials.

6. The apparatus of claim 1 wherein said movable plate is located above said fixed plate and defines a hole therein to accommodate said fluid materials.

7. The apparatus of claim 1 wherein said vibratory means is maintained in vibration at a known amplutide, and said driving force is linearly proportional to a driving voltage, and said driving force is measured by measuring said voltage.

* * * * *